United States Patent [19]

Legendre et al.

[11] 4,245,494

[45] Jan. 20, 1981

[54] INLET SYSTEM FOR DIRECT GAS CHROMATOGRAPHIC AND COMBINED GAS CHROMATOGRAPHIC/MASS SPECTROMETRIC ANALYSIS OF FOOD VOLATILES

[75] Inventors: Michael G. Legendre; Gordon S. Fisher, both of Metairie, La.

[73] Assignee: The United States of America as represented by the Secretary of Agriculture, Washington, D.C.

[21] Appl. No.: 15,507

[22] Filed: Feb. 26, 1979

[51] Int. Cl.³ ............................................. G01N 31/08
[52] U.S. Cl. .................................................... 73/23.1
[58] Field of Search .......................... 73/23.1, 422 GC; 23/232 C; 422/89; 55/67, 197, 386

[56] References Cited

U.S. PATENT DOCUMENTS

| | | | |
|---|---|---|---|
| 2,757,541 | 8/1956 | Watson et al. | 73/23.1 |
| 3,053,077 | 9/1962 | Tracht | 73/23.1 |
| 3,779,066 | 12/1973 | Fore et al. | 73/23.1 |
| 4,003,257 | 1/1977 | Fletcher et al. | 73/23.1 |

OTHER PUBLICATIONS

M. G. Legendre et al., "Practical Device for Unconventional Analysis of Food Volatiles", Journal of American Oil Chemists' Society, vol. 55, pp. 243A, Mar. 1978.

Primary Examiner—Stephen A. Kreitman
Attorney, Agent, or Firm—M. Howard Silverstein; Raymond C. Von Bodungen; David G. McConnel

[57] ABSTRACT

An apparatus for analyzing volatile components from raw or processed food products using either direct gas chromatography or combined direct gas chromatography and mass spectrometry is disclosed. An inlet assembly containing a sample is appropriately affixed to a means of supplying helium carrier gas. Volatiles are driven off the sample and fed to a condenser assembly where the moisture is removed. The resultant moisture free volatiles are fed to a gas chromatograph or combined direct gas chromatograph and mass spectrograph for analysis.

17 Claims, 4 Drawing Figures

INLET SYSTEM FOR DIRECT GAS CHROMATOGRAPHIC AND COMBINED GAS CHROMATOGRAPHIC/MASS SPECTROMETRIC ANALYSIS OF FOOD VOLATILES

BACKGROUND OF THE INVENTION

1. Field of the Invention

This invention relates to an apparatus for analyzing volatile components from raw or processed food products using either direct gas chromatography or combined direct gas chromatography and mass spectrometry.

2. Description of the Prior Art

In recent years, the analysis of food volatiles by direct gas chromatography (GC) has received much attention as described in the following documents:

Brown, D. F., F. G. Dollear and H. P. Dupuy, *JAOCS* 49: 81 (1972).

Dupuy, H. P., S. P. Fore, and L. A. Goldblatt, *JAOCS* 50: 340 (1973).

Fore, S. P., H. P. Dupuy, and J. I. Wadsworth, *Peanut Science* Vol 3, 86 (1976).

Dupuy, H. P., E. T. Rayner, and J. I. Wadsworth, *JAOCS* 53: 628 (1976).

Dupuy, H. P., E. T. Rayner, J. I. Wadsworth, and M. G. Legendre, *JAOCS* 54: 445 (1977).

Jackson, H. W., and D. J. Giacherio, *JAOCS* 54: 458 (1977).

Williams, J. L., and T. H. Applewhite, *JAOCS* 54: 461 (1977).

Zlatkis, A., H. A. Lichtenstein, and A. Tishbee, *Chromatographia*, Vol 6, NO. 2, 67, (1973).

Direct gas chromatographic analysis consists of placing a food sample in a borosilicate glass tubing and introducing this directly into the injection port of a gas chromatograph. Analysis of the number and the magnitude of various volatile materials in the sample is achieved by temperature programming the gas chromatograph, which separates or resolves the volatiles present. This direct (GC) can be further refined to effectively identify such food volatiles by interfacing or "coupling" the gas chromatograph with a mass spectrometer. The latter technique is the most meaningful, since this provides direct information on the actual composition of the food sample. Use of a mass spectrometer, however, requires that essentially all moisture be removed from the volatiles before they are analysed. This has necessitated the minimum use of two-step adsorption-desorption techniques which are critical and time consuming procedures as described in:

Legendre, M. G., H. P. Dupuy, R. L. Ory, and W. O. McIlrath, *J. Agri. Food Chem.* Vol. 26, No. 5, p 1035–1038 (1978).

Fore, S. P., M. G. Legendre and G. S. Fisher, *JAOCS*, Vol 55, No. 5, P 482–485 (May 1978)

The procedures outlined in the two above references are not always successful.

SUMMARY OF THE INVENTION

The instant invention comprises an inlet assembly appropriately affixed to a supply of helium carrier gas. The inlet assembly contains a sample from which the volatiles are removed by heating. The volatiles, after being removed from the sample, are fed into a condenser assembly, which is affixed to the lower end of the inlet assembly, via the carrier gas. The condenser assembly condenses out any moisture from the volatiles. The resultant moisture-free volatile sample is fed into a gas chromatograph and mass spectrometer for analysis. The invention described herein, being a single step closed system, precludes the necessity for complex moisture removing methods. In addition, the direct gas chromatography-mass spectrometry (GC/MS) procedures, current in the art, cannot be used with all types of gas chromatographs, since some instruments do not allow for sample introduction via a glass tubing assembly. The externally mounted closed inlet system of this invention: is compatible with all gas chromatographs; allows for greater flexibility in sample size; provides more uniform and efficient heating of the sample, which, in turn promotes enhanced distillation of food volatiles; and it effectively removes water from such volatiles quickly and easily with a single step closed system operation which requires no interchange of traps for volatiles or moisture, during, between, or after individual analysis.

The specific advantages of this invention are:

(1) The externally mounted inlet system can be constructed to accomodate the desired sample size.

(2) Heating area of the sample is materially increased, thus providing more uniform and efficient heating, to enhance the liberation of volatiles as compared to previously described inlet systems.

(3) It is compatible with all commonly used chromatographs.

(4) It is a single operation, closed system which obviates the need for interchanging traps that have heretofore been necessary to collect volatiles or remove moisture from the volatiles prior to analysis.

DESCRIPTION OF THE PREFERRED EMBODIMENTS

In general, the instant invention comprises three sections: (1) an inlet assembly, (2) a condenser unit, and (3) a six-port rotary valve.

The inlet assembly consists of a stainless steel pipe nipple, whose length will be determined by the general sample size normally introduced. Two stainless steel pipe caps, whose ends are drilled and tapped to accomodate Swagelok fittings, two perforated silicone septa, a heating tape, used for heating the inlet assembly and thus distill off the volatiles, and a stainless steel Quick-Connect fitting to attach the inlet to a supply of carrier of gas.

The condenser assembly consists of stainless steel tubing which is filled with glass wool coated with sodium sulfate and retained at each end with a plug of glass wool. A heating tape is wrapped around the condenser to supply heat for regenerating the sodium sulfate to an anhydrous condition. A copper tubing is coiled around this assembly between the Swagelok fitting nuts at the top and bottom and is supplied with compressed air for cooling the condenser when water is being absorbed from a sample heating in the inlet.

The final element of this invention is a six port rotary valve, No. 8032, supplied by Carle Instruments, Fullerton, Calif. More specifically, in the preferred embodiments, a food sample is supported on or placed between two plugs of volatile-free glass wool in a borosilicate glass tubing about ⅜ in. O.D. by 3⅜ in. long. This tube is inserted into the top of the inlet assembly, and the pipe cap is then hand tightened, positioning the tube between two perforated silicone septa to form a seal on both sides. With the rotary valve in the "injection position," carrier gas is forced to flow down through the sample during heating of the inlet. The volatiles and moisture are swept from the heated sample through the compressed air cooled condenser assembly, where moisture is trapped, and volatiles continue through to the top portion of the (GC) column where they are absorbed. This operation is conducted for a period of about from 10 to 30 minutes depending on the nature of the sample. The rotary valve then is changed to the "run/purge" position, and the (GC) column oven is temperature programmed to resolve the volatile components. While temperature programming is in progress, the inlet assembly is cooled, and the sample tube is removed and replaced with an empty tube to retain the seals and maintain continuity of the carrier gas flow. The condenser assembly is then heated to about 120° C. to 150° C. to drive off moisture through the combined action of the heat and flow of carrier gas. The sodium sulfate in the condenser is thus regenerated to an anhydrous state over a period of about 15 to 30 minutes.

Figures 1, 2:
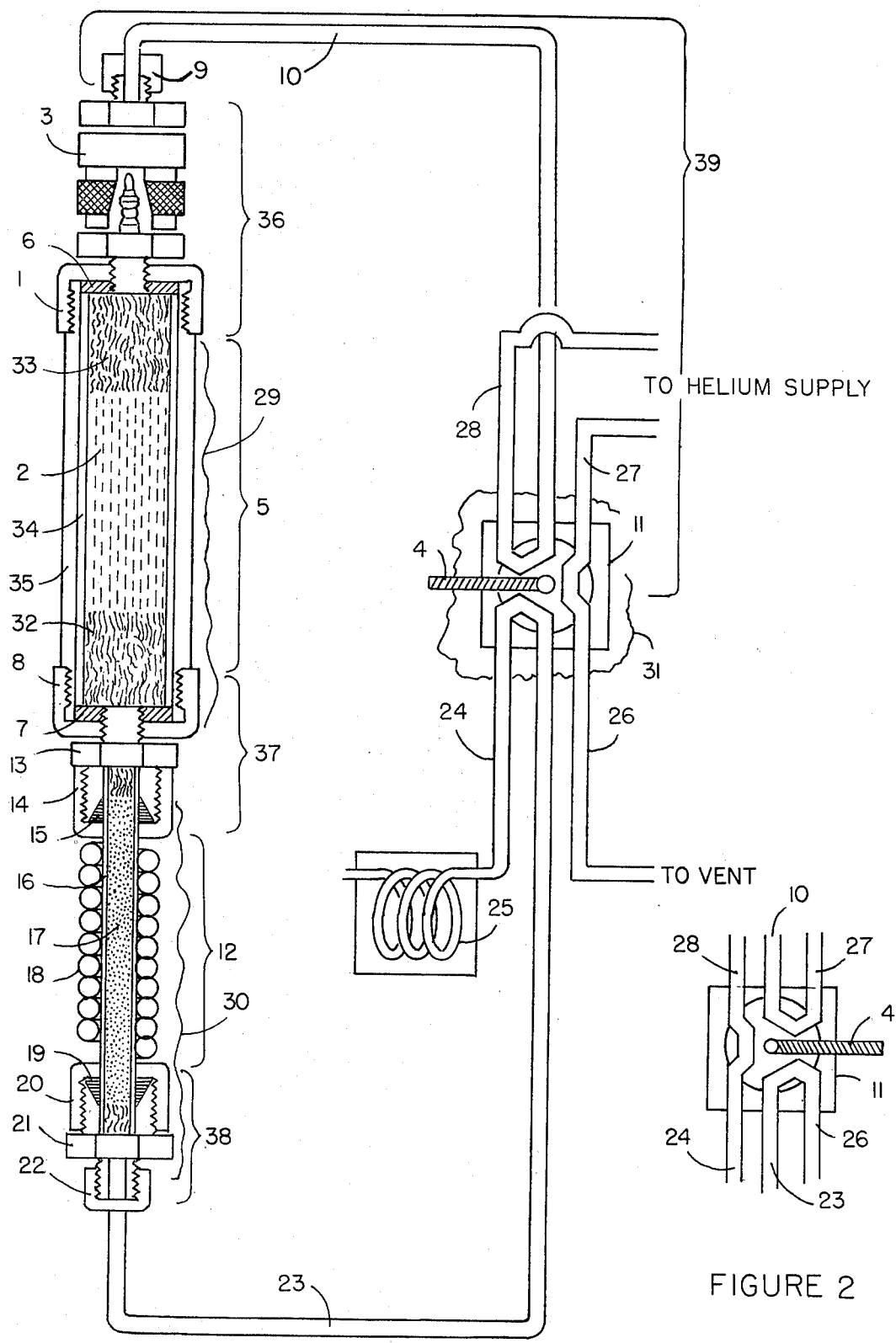
FIG. 1 is a schematic showing the novel components of the invention.
FIG. 2 describes the six port rotary valve in the "Run/Purge" position.

Even more specifically, referring now to FIG. 1 wherein helium supply assembly 39 which comprises a six port rotary valve 11, tubings 27, 28 and 10, and first Swagelok nut 9, forms a means for supplying helium carrier gas to upper inlet connecting assembly 36. Upper connecting assembly 36 comprising upper cap 1 which includes silicone septum 6 and lower part of quick connect 3 affixed to said upper cap 1 is removed from inlet assembly 5 and blank glass tube cartridge (not shown) is removed from inlet 5. Glass liner 34 containing food sample 2 is inserted into cylinder 35 of inlet assembly 5 in place of the blank cartridge. Upper cap 1 is then reinstalled to the upper end of inlet assembly 5 and hand tightened in order to promote a seal on both ends of inlet assembly 5 via silicone septa 6 and 7. Inlet assembly 5 already has the opposing end sealed by lower cap 8 which contains silicone septum 7. Lower cap 8 and silicone septum 7 are never removed except for periodic maintenance. Quick connect 3 is then affixed to mating part of upper cap 1. Stainless tubing 10 is connected to quick connect 3 by means of Swagelok nut 9 and accompanying ferrules (not shown). Stainless steel tubing 10, fed by either tubing 27 or 28 depending on rotary valve 11's position, is part of a six port rotary valve 11 which is connected to an external helium supply (not shown).

Inlet assembly 5 can be heated by means of heating tape 29 which wraps externally around inlet assembly 5 and which is activated or deactivated by means of a variable voltage supply (not shown). Six port rotary valve 11 and tubing 23 are heated by means of heating tape 31 which also wraps externally around said elements.

On the opposing or lower end of inlet assembly 5, condenser assembly 12 is affixed to inlet assembly 5 by means of lower inlet connecting assembly 37 which comprises lower cap 8, Swagelok reducer 13, second Swagelok nut 14, Vespel ferrule 15 and septum 7. Vespel ferrule 15 serves to seal moisture absorption chamber 16 when connected to inlet assembly 5. Moisture absorption chamber 16 contains volatile free glass wool 17 which is coated with anhydrous sodium sulfate forming a matrix. Moisture absorption chamber 16 can be either heated or cooled. When cooled, moisture absorption chamber 16 is wrapped by cooper tubing coil 18 which is functionalized by circulating a cooling fluid therethrough which can be water or air. Thus, copper tubing coil 18 is permanently affixed around moisture absorption chamber 16. When heated, heating tape 30 which is externally wrapped around the outer surface of copper tubing coil 18, forms a covering for moisture absorption chamber 16. Copper coil 18 is easily deactivated during heating, and heating tape 30 is easily deactivated during cooling. Thus, condenser assembly 12 comprises moisture absorption chamber 16, copper cooling coil 18, and heating tape 30. Stainless steel tubing 23 is connected to condenser assembly 12 by means of lower condenser connecting assembly 38 comprising Vespel ferrule 19, third Swagelok nut 20, Swagelok reducer 21, fourth Swagelok nut 22, and accompanying ferrules (not shown). Tubing 23 when connected to tubing 24 is a means for directing sample volatiles to (GC) column 25, and forms part of six port rotary valve 11.

Tubing 24 which is also part of six port rotary valve 11 is connected to the inlet side of gas chromatographic column 25. The exit side or detector side of gas chromatographic column 25 can be connected to a mass spectrometer (not shown) by means of an appropriate separator (not shown). Stainless steel tubing 26 which also forms part of a six port rotary valve 11 serves as a vent to the atmosphere.

Temperature monitoring can be achieved by means of thermocouples (not shown) which can be attached to inlet assembly 5, condenser assembly 12 and six port rotary valve 11.

Moisture absorption chamber 16 is prepared by packing chamber 16 with volatile-free glass wool and subsequently dripping a saturated aqueous solution of sodium sulfate therethrough. After the packed glass wool is totally covered with sodium sulfate solution, the resultant chamber is dried out in an oven until all the moisture is removed leaving a coating of anhydrous sodium sulfate on the glass wool.

Samples for analysis are prepared as follows: For solid or Semi-solid samples, glass liner 34 is packed with lower volatile-free glass wool plug 32, ground food sample 2, and upper volatile-free glass wool plug 33, and is inserted into inlet assembly 5. For liquid samples, glass tube 34 is totally packed with volatile-free glass wool forming a matrix, and the sample to be analyzed is dripped onto the glass wool matrix prior to insertion of glass tube 34 into assembly 5.

When not in operation the apparatus is maintained with a blank cartridge in inlet assembly 5 and with helium flowing through the entire apparatus to provide a constant purge to maintain stable anhydrous condition in the moisture absorbing chamber.

In operation, a sample is prepared in glass tube 34, as described supra, and inserted into inlet assembly 5. Upper cap 1 is affixed to the inlet end of assembly 5 and hand tightened, thus forming a seal between silicone septa 6 and 7. Quick connect 3 is attached to its adjacent mating surface of upper cap 1.

Six port rotary valve 11 is switched into "inject" position via handle 4. Handle 4 is positioned on six port rotary valve 11 in the "inject" position so that stainless tubing 10 is supplied with helium from tubing 28 causing tubing 23 to direct the volatiles from the sample which is in the inlet assembly 5 through inlet assembly 5 through condenser assembly 12 via tube 23 and 24, and delivering them to (GC) column 25. Heating tape 29 is activated during this time to maintain the appropriate temperature.

Concurrently, condenser assembly 12 is maintained at temperature via copper cooling coils 18. Subsequently, the combination of heat and helium flow thru the sample contained in the inlet assembly 5 for a period of about 10 to 30 minutes. During this time the volatiles are collected on the head of the (GC) column. Rotary valve 11 is then switched into the "run/purge" position via handle 4 isolating inlet assembly 5 and the sample from gas chromatographic column 25.

Figure 3:
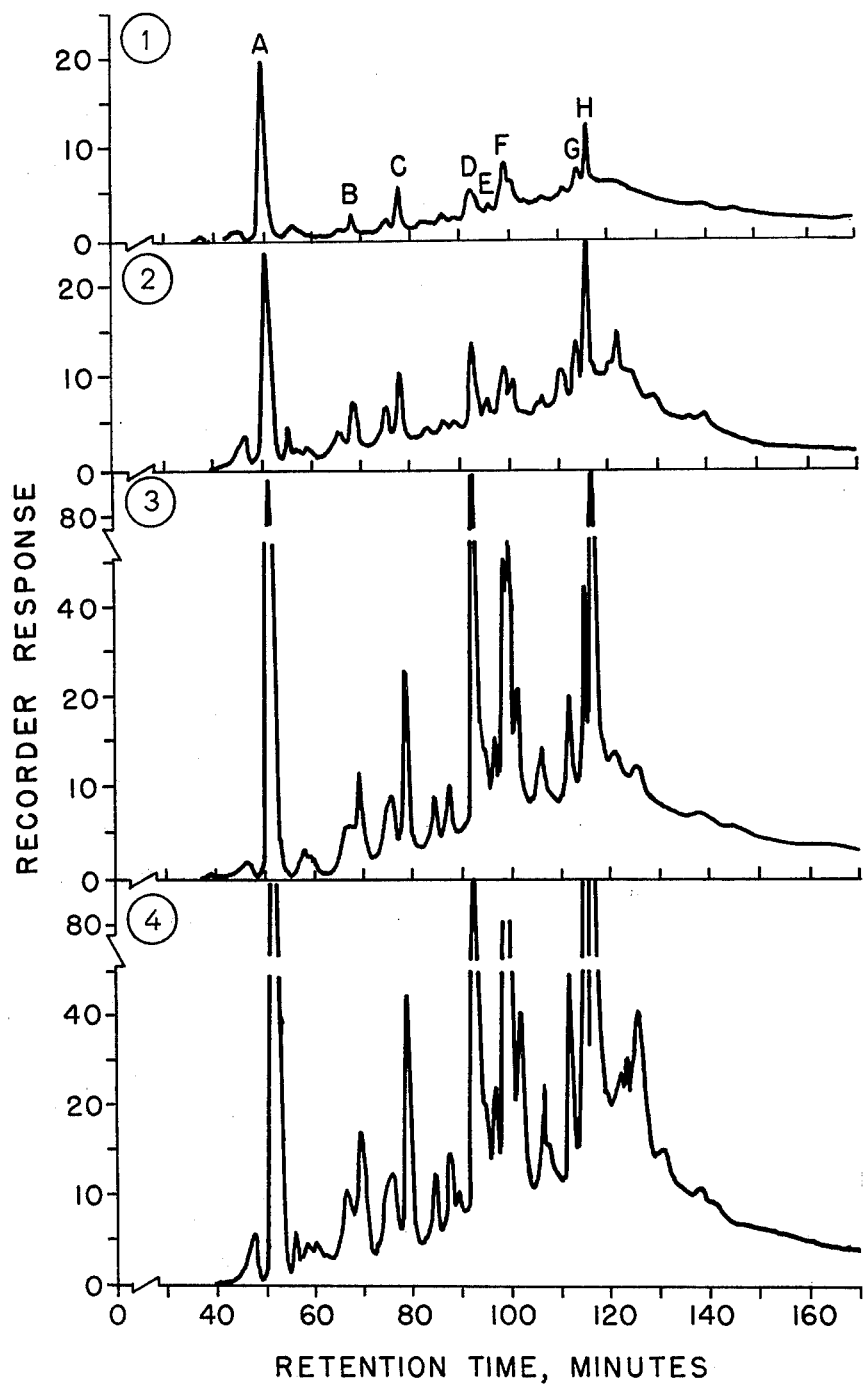
FIG. 3 is a set of chromatograms showing the differences between high and low quality vegetable oils.

Handle 4 is positioned on six port rotary valve 11 in the "run/purge" position to direct helium in tubing 28 directly to tubing 24 and subsequently (GC) column 25, thereby isolating the inlet assembly 5 and condenser assembly 12 from the (GC) column 25. Now tubing 27 is connected to tubing 10 and tubing 23 is connected to tubing 26 which will vent moisture and helium carrier gas to the atmosphere. The (GC) column is then temperature programmed thereby resolving the volatile components. At this time the inlet assembly heater 29 is shut off, the sample liner is replaced with a blank liner, then cooling material is shut off from condenser assembly 12 and heating tape 30 is turned on, and condenser assembly 12 is maintained at about 120° to 150° C. for about 10 to 20 minutes. The heater of the condenser assembly 12 is then turned off and allowed to cool to room temperature via condenser coil 18. Thus the $Na_2SO_4$ in the moisture absorbing chamber 16 is rendered anhydrous and ready for the next sample. As the volatiles are resolved in (GC) column 25, components arrive at the (GC) detector (not shown) and a signal is outputed to a strip chart recorder (not shown). Thus chromatograms are obtained as shown in FIGS. 2 and 3.

The following examples are presented to illustrate the utility of this invention, but do not limit its scope or application to the examples cited.

EXAMPLE 1

Analysis of Volatiles in Soybean Oils

Two different quality soybean oils were analyzed by combined direction GC/MS analysis using (1) the older, traditional method for combined direct GC/MS analysis, and (2) the novel, single step, external and closed inlet system described in this invention. Chromatograms 1 and 2, shown in FIG. 3, represent analysis of a high quality, bland (low volatiles content) soybean oil. Chromatogram 1 was made using the traditional method of combined GC/MS analysis, which consisted of the following:

A 3⅜ in. length of ⅜ in. O.D. boroxilicate glass tubing was packed wih volatile-free glass wool, loose enough to permit diffusion of oil throughout the packing, but tight enough to prevent seepage of the sample from the liner onto the (GC) column. Clearance of ¼ in. was allowed at the bottom of the liner and ½ in. at the top. A 600 mg. sample of soybean oil was added at the top. The septum nut, septum and retainer nut of the (GC) were removed, and the liner containing the sample was inserted in the inlet of the (GC) on top of the silicone O-ring. When the retainer nut was tightened above the upper lip of the liner, a seal was formed between the base of the inlet and the lower lip of the liner. On closing the inlet system with the septum and septum nut, the carrier gas was forced to flow upward and then down through the sample, thus eluting the volatiles from the sample as the carrier was swept through the heated portion of the liner. The volatiles were thereby transferred to the top of the (GC) column, where subsequent temperature programming resolved them and mass spectral analysis characterized the more prominent peaks.

Chromatogram 2 represents combined GC/MS analysis of the same soybean oil using the novel, single step closed external inlet system of the instant invention. The oil sample size, temperatures employed, and carrier gas flow were all the same used for chromatogram 1, and the general mechanics of operation described earlier under "Application" were followed. It is important to note that in the analysis of vegetable oils, water is not an essential component required to elute volatiles from the product as it frequently is with other commodities. Thus, in these two chromatograms, it was not necessary to use a moisture trap to effect the desired MS analysis. It can be clearly seen however, that although the novel sodium sulfate trap of this invention was not required for these oils, the peaks produced by the design of our invention, shown in Chromatogram 2, are greater in number and magnitude, indicating a higher level of sensitivity. This is due to the more uniform and efficient heating provided by our inlet system, and the closed nature of the assembly, which retains more volatiles.

Chromatograms 3 and 4 of FIG. 3, similarly show the analysis of a poorer grade (higher volatiles content) soybean oil. Chromatogram 3, FIG. 3 was obtained by the traditional method of combined GC/MS analysis, and chromatogram 4, FIG. 3 shows the results of analyzing the same oil using the novel component systems of the instant invention. As noted for the previous oil, the volatile peaks obtained in chromatogram 4, using the process of our invention, are more abundant, appear with greater intensity and are more clearly defined. Again, this effect is attributable to the increased efficiency and uniformity of heating which is inherent in the construction of our novel one step, closed inlet system.

EXAMPLE 2

Analysis of Corn-soy Food Blends

Figure 4:
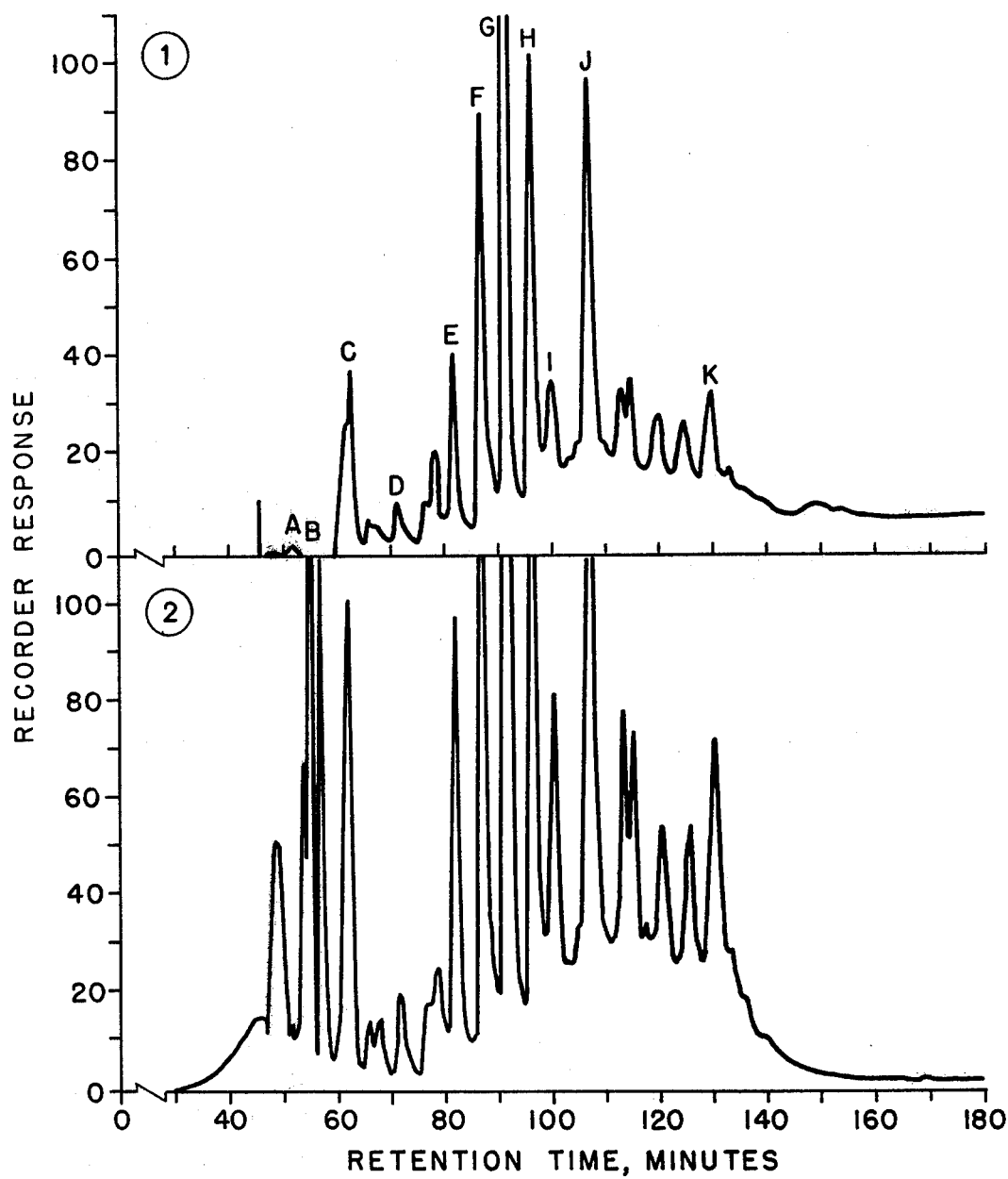
FIG. 4 is a set of chromatograms of a corn-soy food blend.

A sample of corn-soy food blend was analyzed by combined direct GC/MS, using (1) the older, traditional method for direct combined GC/MS analysis, and (2) the novel, single step, external inlet system described in the instant invention. FIG. 4 shows a comparison of results obtained. Chromatogram 1, FIG. 4, was obtained using the traditional method in the following manner: A Tracor Model 222 GC interfaced with Hewlett Packard (quadrapole) mass spectrometer were the instruments used. A 1000 mg. sample of corn-soy food blend was placed in a 3⅜ length of ⅜ in. borosilicate glass tubing and packed on both ends with glass wool. A clearance of ½ in. was allowed at the bottom of the liner. The septum nut, septum, and retainer nut of the GC were removed, and the liner containing the sample was inserted in the inlet of the (GC) on top of a teflon O-ring. When the retainer nut was tightened above the upper rim of the liner, a seal was formed between the base of the inlet and the lower rim of the liner. On closing the inlet system with the septum and septum nut, the carrier gas (helium) was forced to flow upward and then down through the sample. Volatiles were readily removed from the sample as the carrier gas (helium) swept through the heated liner (160° C.), and were absorbed over a period of 30 minutes onto another sample glass liner, which was attached on the bottom of the (GC) inlet with a ⅜ in. Swagelok adapter and teflon ferrules. This extra liner is composed of a volatile-free glass wool "sandwich" containing 0.4 g of Porapak P (GC) absorbent packing, and is wrapped with a damp towel to provide cooling as the volatiles are adsorbed by the Porapak P. Moisture and possibly some low molecular weight volatiles pass through this "trap" and are dissipated into the air. Frequently if too much moisture is present in the sample the Porapak P liner does not remove sufficient water to permit mass spectral analysis. The Porapak P liner, containing most of the adsorbed volatiles, is then inserted into the GC inlet at 160° C. to desorb the volatiles and the oven is temperature programmed at 4° per minute for 45 minutes to resolve the volatiles into the profile pattern shown in chromatogram 1. Final temperature hold was at 220 until the column was clear.

Chromatogram 2, FIG. 4, was obtained from a sample of the same corn-soy blend used for producing chromatogram 1, but in this instance the novel, external single step, closed inlet system of the instant invention was employed. The instruments and conditions of operation (temperature, time, etc.) were the same as those described for chromatogram 1, but the inovative system of this invention as shown in FIG. 1 was applied in the general manner described previously under "Application." Once again the greater sensitivity of our novel, single step, closed inlet system is apparent. A greater number of volatile peaks of higher magnitude are evident in chromatogram 2, especially in the low molecular weight volatile compound range which appear at shorter retention times. A comparison of chromatograms 1 and 2 clearly indicate that the higher, more volatile, compounds, often key factors in flavor and aroma, are more effectively detected by the process of our invention. The greater efficiency of detection, and reduced possibility of volatiles loss resulting from a closed system, and the one step simplicity of operations which shortens analysis time characterize the salient features of this novel invention.

Although this invention is not limited to any specific dimensions or materials, assemblies were constructed using the following parts. Referring to FIG. 1, the upper connecting assembly 36 comprising upper cap 1 (¼" stainless steel pipe cap), silicone septum 6 (which is cut to fit snugly inside pipe cap) and quick connect 3 (1/16" Swagelok Quick Connect fitting) which is affixed to tubing 10 (part of six port rotary valve 11, Carle Instruments, part #8032) by means of first nut 9 (1/16" Swagelok stainless steel nut) and its associated ferrules (1/16" Swagelok stainless steel ferrules, not shown), is connected to inlet assembly 5, which is comprised of cylinder 35 (¼"×3" stainless steel pipe nipple) wrapped by heating tape 29 (⅜"×12" Briskeat heating tape #BM-1⅜) and contains glass liner 34 (⅜" O.D.×3⅜" Borosilicate glass tube), and glass wool plugs 32 and 33, and sample 2 therein. Inlet assembly 5 is connected on its lower or exit side to condenser assembly 12, which comprises chamber 16 (¼"×2½" stainless steel tubing), cooling coil 18 (⅛" copper tubing) and sodium sulfate-coated glass wool 17 (Corning Glass glass wool, anhydrous sodium sulfate from Mallinckrodt Chemicals), and is wrapped with heating tape 30 (same as heating tape 29), by means of lower inlet connecting assembly 37, which is comprised of lower cap 8 (same as cap 1) silicone septum 7 (same as septum 6), reducer 13 (¼" to 1/16" Swagelok stainless steel reducing union), second nut 14 (¼" Swagelok stainless steel nut) and Vespel ferrule 15 (¼" Vespel ferrule). Condenser assembly 12 is affixed on its lower end to tubing 23 (part of six port rotary valve 11) by means of lower condenser connecting assembly 38 which comprises third nut 20 (same as nut 14), Vespel ferrule 19 (same as Vespel ferrule 15), reducer 21 (same as reducer 13), fourth nut 22 (same as nut 9) and its associated ferrules (1/16" Swagelok stainless steel ferrules, not shown). Tubing 23 and valve 11 are wrapped with heating tape 31 (same as heating tape 29).

We claim:

1. An apparatus for analyzing volatile components from raw or processed food products using either direct gas chromatography or combined direct gas chromatography and mass spectrometry comprising in combination the following:
   (a) an inlet assembly containing a sample, said assembly designed to remove volatiles from said sample, and said volatiles to subsequently be analyzed;
   (b) a helium supply assembly to supply helium carrier gas to said inlet assembly via an upper inlet connecting assembly, said carrier gas to transport the volatiles from the inlet assembly to and through a condenser assembly;
   (c) said condenser assembly affixed to the lower end of the inlet assembly by means of a lower inlet connecting assembly, said condenser assembly used to condense the absorb sample moisture from the volatiles thus rendering the volatiles moisture-free;
   (d) a means for directing sample volatiles from said condenser assembly to a gas chromatographic column, said sample volatile directing means affixed on its intake end to the lower or outlet end of said condenser assembly via a lower condenser connecting assembly and on the exhaust end to a gas chromatographic column.

2. The apparatus of claim 1 wherein the upper inlet connecting assembly comprises:
   (a) a cap;
   (b) a silicone septum installed in said cap;
   (c) a quick connect affixed to said cap.

3. The apparatus of claim 1 wherein the inlet assembly containing the sample comprises:
   (a) a glass liner packed with a food sample between upper and lower glass wool plugs.

4. The apparatus of claim 1 wherein the inlet assembly containing the sample comprises:
   (a) a glass liner packed with a food sample on a glass wool matrix.

5. The apparatus of claim 1 wherein the helium supply assembly comprises:
   (a) a six port rotary valve communicating with said upper inlet connecting assembly via stainless steel tubing which is affixed to the upper inlet connecting assembly by means of a first nut.

6. The apparatus of claim 1 wherein the inlet assembly includes a means of heating the sample.

7. The apparatus of claim 6 wherein the means of heating the inlet assembly is a heating tape.

8. The apparatus of claim 1 wherein the condenser assembly comprises:

(a) a moisture absorption chamber packed with a sodium sulfate-coated glass wool matrix to absorb moisture;

(b) said absorption chamber wrapped by a copper coil through which is circulated a cooling fluid.

9. The apparatus of claim 8 including means of heating said condenser assembly.

10. The apparatus of claim 9 wherein the means of heating the condenser assembly is a heating tape.

11. The apparatus of claim 9 including a means of heating the six port rotary valve.

12. The apparatus of claim 11 including a means of heating the stainless steel tubing.

13. The apparatus of claim 1 wherein the lower inlet connecting assembly comprises:

(a) a second nut affixed and sealed to a reducer by means of a ferrule therebetween, said reducer affixed to a lower cap which is affixed to the lower end of said inlet assembly.

14. The apparatus of claim 1 wherein the lower condenser connecting assembly comprises:

(a) a fourth nut which is affixed and sealed to a reducer which is affixed to a third nut affixed to the exit end of said condenser assembly, said fourth nut also affixed to the means for directing sample volatiles.

15. The apparatus of claim 14 including a ferrule located between the reducer and the second nut to form a seal between the condenser assembly and the lower condenser connecting assembly.

16. The apparatus of claim 1 wherein the means for directing sample volatiles comprises:

(a) a six port rotary valve communicating with said lower condenser connecting assembly via stainless steel tubing and also communicating with an inlet end of a gas chromatographic column via stainless steel tubing.

17. The apparatus of claim 16 wherein the six port rotary valve includes a means of redirecting the flow of carrier gas and sample volatiles.

* * * * *